United States Patent
Sakumura et al.

(10) Patent No.: US 9,341,583 B2
(45) Date of Patent: May 17, 2016

(54) CORRECTION INFORMATION GENERATION METHOD AND CORRECTION INFORMATION GENERATION APPARATUS

(71) Applicant: Rigaku Corporation, Akishima-shi, Tokyo (JP)

(72) Inventors: Takuto Sakumura, Hachioji (JP); Yasukazu Nakaye, Ome (JP)

(73) Assignee: RIGAKU CORPORATION, Tokyo (JP)

( * ) Notice: Subject to any disclaimer, the term of this patent is extended or adjusted under 35 U.S.C. 154(b) by 0 days.

(21) Appl. No.: 14/523,226

(22) Filed: Oct. 24, 2014

(65) Prior Publication Data
US 2015/0146960 A1    May 28, 2015

(30) Foreign Application Priority Data

Nov. 22, 2013  (JP) ................... 2013-242291

(51) Int. Cl.
*G06K 9/00*  (2006.01)
*G01N 23/207*  (2006.01)

(52) U.S. Cl.
CPC ........ *G01N 23/207* (2013.01); *G01N 2223/303* (2013.01)

(58) Field of Classification Search
None
See application file for complete search history.

(56) References Cited

U.S. PATENT DOCUMENTS

| 6,350,985 | B1 | 2/2002 | Rodricks et al. |
| 7,095,039 | B2 | 8/2006 | Murakoshi |
| 7,136,454 | B2 | 11/2006 | Gerndt et al. |
| 2004/0061081 | A1 | 4/2004 | Murakoshi |
| 2004/0113107 | A1 | 6/2004 | Sakabe |
| 2005/0259790 | A1 | 11/2005 | Gerndt et al. |
| 2006/0291711 | A1* | 12/2006 | Jabri ............ G06T 11/005 382/132 |
| 2009/0101798 | A1* | 4/2009 | Yadid-Pecht ...... H04N 5/3532 250/208.1 |
| 2010/0127184 | A1* | 5/2010 | Balakin ............ A61N 5/1049 250/396 R |

FOREIGN PATENT DOCUMENTS

| JP | 2004-128695 A | 4/2004 |
| JP | 2004-191789 A | 7/2004 |
| WO | WO 00/65374 A1 | 11/2000 |

* cited by examiner

*Primary Examiner* — Stephen R Koziol
*Assistant Examiner* — Amandeep Saini
(74) *Attorney, Agent, or Firm* — Birch, Stewart, Kolasch & Birch, LLP

(57) ABSTRACT

A correction information generation method and a correction information generation apparatus enabling easy Flat-Field Correction operation without special accessory equipment are provided. The correction information generation method for performing Flat-Field Correction of X-ray detection sensitivity on a pixel detector, includes the steps of: moving the relative position of a detector 130 with respect to an incident X-ray having a cross-sectional beam shape traversing a detection surface so that the whole of the detection surface is irradiated with the incident X-ray in total time and each of pixels arranged in the moving direction is uniformly irradiated; and generating information for correcting the sensitivity of a pixel based on an intensity value detected for a given energy band of the incident X-ray.

7 Claims, 8 Drawing Sheets

CORRECTION INFORMATION GENERATION METHOD AND CORRECTION INFORMATION GENERATION APPARATUS

BACKGROUND OF THE INVENTION

1. Field of the Invention

The present invention relates to a correction information generation method and a correction information generation apparatus for performing Flat-Field Correction of X-ray detection sensitivity on a pixel detector.

2. Description of the Related Art

It is called Flat-Field Correction to correct sensitivity that is different by pixel in a pixel detector so that actual sensitivity becomes virtually uniform. Flat-Field Correction of the pixel detector, which is carried out by normalizing the values of counts read by each pixel, is effective to one or more dimensional detectors.

When a detector is irradiated with a uniform X-ray, readout channels of each pixel would measure the same number of counts. However, difference in sensitivity parameters by each pixel will occur due to difference in sensitivity, and the number of counts will differ by pixel. In order to reduce such an effect, Flat-Field Correction is carried out.

In a standard correction procedure, counts of all pixels are measured by radiating uniform X-rays to a detector and the measured values are normalized. That is, by ensuring that the whole of the detection surface is irradiated with X-rays at the same intensity by arranging an X-ray beam source and the detector while keeping the long distance between them to make X-rays as uniform as possible, and correction coefficients are calculated based on the premise that the obtained values of counts should actually have the same intensity.

FIG. 8 is a schematic perspective view illustrating a conventional method for correcting sensitivity of a detection pixel. As illustrated in FIG. 8, in the above described procedure, the detector is irradiated with an X-ray from an X-ray beam source through a beam pathway by a helium chamber designed so as to minimize spatial scattering of the X-ray.

On the other hand, there are also patent documents proposing a correction method. In Patent Document 1, as a conventional technology for correcting time degradation of a reference light source, a method, which carries out a correction procedure using data when an accumulative phosphor sheet is uniformly exposed with X-rays, is disclosed. In Patent Document 2, a method, which carries out sensitivity correction by a step of uniformly exposing an accumulative phosphor sheet by transferring the sheet while shuttling an X-ray generation apparatus in a width direction, is disclosed. In Patent Document 3, a method, which reduces dead pixels by the steps of recording a first data set, then, sliding a detection face to record a second data set, and superimposing the second dataset on the first dataset, is disclosed.

PATENT DOCUMENTS

Patent Document 1: JP-A 2004-128695
Patent Document 2: JP-A 2004-191789
Patent Document 3: US patent application publication No. 2005/0259790

However, it is difficult to perform above-mentioned Flat-Field Correction of a detection pixel at the user side by attaching dedicated equipment enabling Flat-Field Correction in an X-ray diffractometer in view of the cost and the space for the correction equipment. Further, for example, as a technological problem, the correction coefficient may deviate depending on the temperature during measurement. For example, in a case where an apparatus corrected at 25° C. is used under an environment of 35° C., it is better to carry out correction at the site where the apparatus is used.

SUMMARY OF THE INVENTION

The present invention, which is made in view of such a situation, has an object to provide a correction information generation method and a correction information generation apparatus enabling Flat-Field Correction operation easily without special accessory equipment.

(1) In order to achieve the above-mentioned object, the correction information generation method of the present invention for performing Flat-Field Correction of X-ray detection sensitivity on a pixel detector is characterized by including the steps of: moving the relative position of a detector with respect to an incident X-ray having a cross-sectional beam shape traversing the detection surface so that the whole of the detection surface is irradiated with the incident X-ray in total time and each of pixels arranged in the moving direction is uniformly irradiated; and generating information for correcting the sensitivity of a pixel based on an intensity value detected for a given energy band of the incident X-ray.

Therefore, Flat-Field Correction operation without special accessory equipment is easily enabled, thus, even with an X-ray diffractometer already used, Flat-Field Correction operation is easily enabled at the site.

(2) Further, the method for generating correction information of the present invention is characterized in that the incident X-ray is a diffraction X-ray, and the relative moving direction of the detector with respect to the incident X-ray is a diffraction angle direction of the diffraction X-ray.

This enables a virtual flat-field irradiation using a uniform high-intensity X-ray. By irradiating the high-intensity X-ray, Flat-Field Correction operation is more effectively enabled in a short time.

(3) Further, the method for generating correction information of the present invention is characterized in that the incident X-ray is a Debye ring. This enables the virtual flat-field irradiation using the uniform high-intensity X-ray.

(4) Further, the correction information generation method of the present invention is characterized in that the information for correcting the sensitivity of the pixel under an assumption that each of the pixels arranged in the moving direction is irradiated at uniform integrated intensity. This enables sensitivity correction for every pixel in a simple way without carrying out spherical correction.

(5) Further, the method for generating correction information of the present invention is characterized in that the information for correcting the sensitivity of the pixel is generated under an assumption that the detected intensity value is spherically corrected and the whole of the detection surface is irradiated at uniform integrated intensity. This enables more precise correction using the whole of the detection surface.

(6) Further, the method for generating correction information of the present invention is characterized in that the information for correcting the sensitivity of the pixel is a table including a correction coefficient of each of the pixels. This enables easy sensitivity correction for every pixel by multiplying detected intensity read out from the table.

(7) Furthermore, the correction information generation apparatus of the present invention, which is an apparatus for generating correction information for performing Flat-Field Correction of X-ray detection sensitivity on a pixel detector, characterized by including a correction information generation section that generates information for correcting the sensitivity of a pixel based on an intensity value detected for a given energy band of the incident X-ray by moving the relative position of a detector with respect to the incident X-ray having a cross-sectional beam shape traversing the detection surface so that the whole of the detection surface is irradiated with the incident X-ray in total time and each of the pixels arranged in the moving direction is irradiated uniformly. This enables easy Flat-Field Correction operation without special accessory equipment.

According to the present invention, Flat-Field Correction operation can be easily performed without special accessory equipment, and even with an already used X-ray diffractometer, Flat-Field Correction operation is easily enabled at the site.

DETAILED DESCRIPTION OF THE INVENTION

Next, embodiments of the present invention will be described with reference to drawings. In order to facilitate understanding of description, in each drawing, the same reference number is attached to the same component and duplicated description will be omitted.

BEST MODES FOR CARRYING OUT THE INVENTION (X-Ray Diffractometer)

Figure 1:
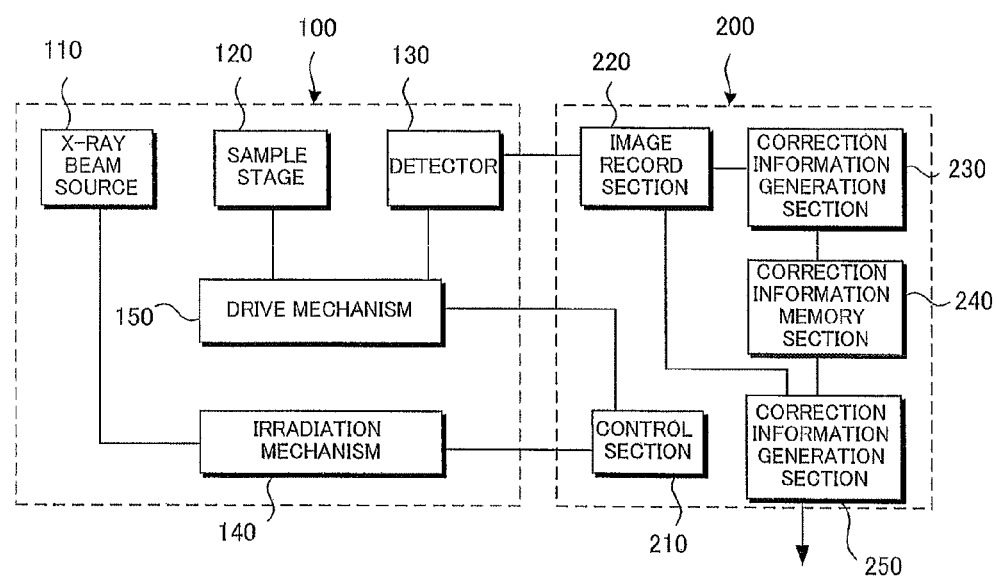
FIG. 1 is a block diagram illustrating the configurations of an X-ray diffractometer and an apparatus for generating correction information.
Figure 2:
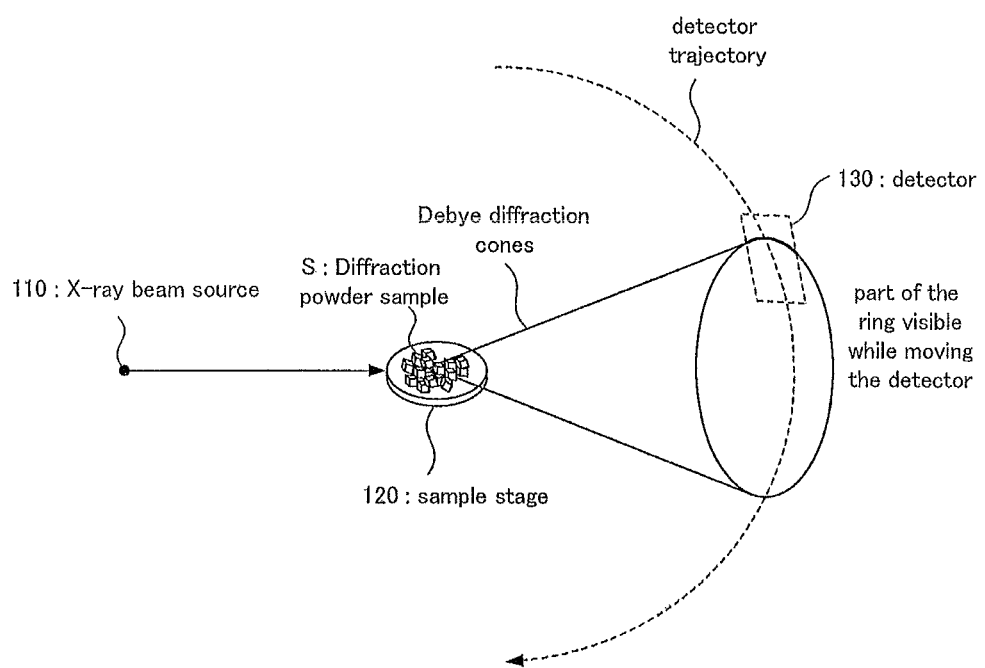
FIG. 2 is a perspective view illustrating the configuration of the X-ray diffractometer.

FIG. 1 is a block diagram illustrating configurations of an X-ray diffractometer 100 and a correction information generation apparatus 200. FIG. 2 is a perspective view illustrating the configuration of the X-ray diffractometer 100. As illustrated in FIGS. 1 and 2, the X-ray diffractometer 100 includes an X-ray beam source 110, a sample stage 120, a detector 130, an irradiation mechanism 140, and a drive mechanism 150.

The X-ray beam source 110 consists of an X-ray tube and emits characteristic X-rays such as Cu and Mo. Monochromatized characteristic X-rays are made into parallel beams having a given diameter by a collimator or the like, and then irradiated to a polycrystalline sample S. The irradiated X-rays are scattered around the sample S at an angle 2θ as diffraction X-rays diffracted by the polycrystalline sample S and enter the detection surface of the detector 130.

The sample stage 120 rotatably holds powder crystals as a sample S. As the sample S, for example, silicon or alumina powder is used. When a silicon powder sample is used, diffraction X-ray of a high intensity is obtained, and when an alumina powder sample is used, a diffraction X-ray with high uniformity in intensity is obtained. The sample stage 120 may be one which rotates by an angle θ while being interlocked with 2θ-rotation of the detector 130, but, preferably it is one which rotates independently from the detector 130 so that a uniform diffraction X-ray is generated.

Although a diffraction X-ray to be used is not limited in particular, a diffraction X-ray from a wide-angled crystalline plane is likely to become a straight line on the detection surface, thereby making correction easy. Further, even when diffraction angles of two diffraction X-rays are close to each other, uniform irradiation is enabled by passing both X-rays through the detection surface.

The detector 130 detects an incident X-ray having a cross-sectional beam shape traversing its detection surface. The detector 130, which is a pixel detector, may be a one-dimensional detector, but, preferably a two-dimensional detector. Specifically, the detector 130 is preferably a wavelength dependent two-dimensional detector capable of identifying energy.

The one-dimensional detector is an X-ray detector having position resolution of X-ray intensity on a straight line. For example, the one-dimensional detector can be formed by arranging a plurality of minute X-ray photo acceptance units whose X-ray is detectable in a shape of a straight line. The two-dimensional detector is an X-ray detector having position resolution of X-ray intensity on a plane. For example, the two-dimensional detector can be formed with a semiconductor X-ray detector which is configured by arranging a plurality of minute X-ray photo acceptance units on a plane and can detect an X-ray per pixel and output a signal per pixel. As examples of such a semiconductor photo acceptance unit, there are CCD and CMOS.

The detector 130 can move the relative position of the detector 130 with respect to an incident X-ray so that the whole detection surface may be irradiated with the X-ray in total time. Further, the relative position of the detector 130 with respect to the incident X-ray can be moved along the moving direction of the X-ray to the detector 130 so that each pixel of the detector 130 may be irradiated at the same integrated intensity.

Specifically, it is preferable that the detector 130 is supported so as to be movable at a constant speed on a circle around the sample S in the direction of a diffraction angle while detecting a diffraction X-ray. As an incident X-ray to be irradiated to the detector 130, a scattered beam of an amorphous carbon may be used, but, in this case, intensity becomes smaller than the case of a diffraction X-ray. The rotation arm of a goniometer can be used for movement of the detector 130, for example. For controlling the movement of the detector 130, the scanning function in usual measurement of a diffraction X-ray can be used as it is.

The irradiation mechanism 140, which is configured with a power supply and circuits, controls irradiation of an X-ray from the X-ray beam source 110. The drive mechanism 150 controls the rotation of the sample stage 120, and the movement of the detector 130. In a case of using a diffraction X-ray, the detector 130 is moved in the direction of the diffraction angle.

The above-mentioned configuration can be applied even to an X-ray apparatus for factory lines of a semiconductor. A direct beam emitted from the X-ray beam source 110 is attenuated by an attenuator and is narrowed down by a slit into a beam having a thin line shape in cross section, which is irradiated to the detector 130. In this case, although beams in wide energy bands are included in the direct beam, it is only necessary to detect a beam in an energy band necessary for the detector 130 side.

(Correction Information Generation Apparatus)

The correction information generation apparatus 200 carries out Flat-Field Correction of X-ray detection sensitivity to the detector 130 by the steps of recording obtained image data of uniform irradiation, and generating correction information using the recorded image data. As illustrated in FIG. 1, the correction information generation apparatus 200, which is constituted by, for example, servers, includes a control section 210, an image record section 220, a correction information generation section 230, correction information memory section 240, and a correction section 250.

The control section 210 enables uniform X-ray irradiation to the detector 130 by the steps of: controlling the irradiation mechanism 140 and the drive mechanism 150; and interlocking the irradiation mechanism 140 and the drive mechanism 150. X-ray beam source 110 emits a given X-ray to irradiate the sample S, then the detector 130 is moved for a given distance on a circle and the sample stage 120 is rotated.

The image record section 220 records the image data of intensity distribution, which is obtained by the detector 130, as it is. In that case, the number of counts (intensity value) of X-rays detected by the detector 130 for a given energy band is recorded.

The correction information generation section 230 generates correction information based on the number of counts of X-rays detected for a given energy band. Correction information is information for correcting the sensitivity of each pixel of the detector 130, for example, it is a table including a correction coefficient of each pixel. Therefore, Flat-Field Correction information with respect to a given energy can be generated, thus, enabling easy Flat-Field Correction operation in even an X-ray diffractometer at the site.

The correction coefficient of a specific pixel is obtained, for example, by the steps of calculating an average value among pixels including the specific pixel where correction coefficients should be the same one; and carrying out the calculation: (average value)/(the number of counts of the specific pixel). In addition, as the number of counts, the number of counts obtained by subtracting background from obtained image data is used, and scattering of asymmetric primary light is removed.

The correction information memory section 240 memorizes generated correction information, such as a table. The correction section 250 reads out correction information memorized in the correction information memory section 240, and performs Flat-Field Correction on image data recorded during an actual experiment using the correction information and outputs the resultant image data. The outputted image data is transferred to, for example, a user's PC.

(Flat-Field Correction Method)

Figure 3:
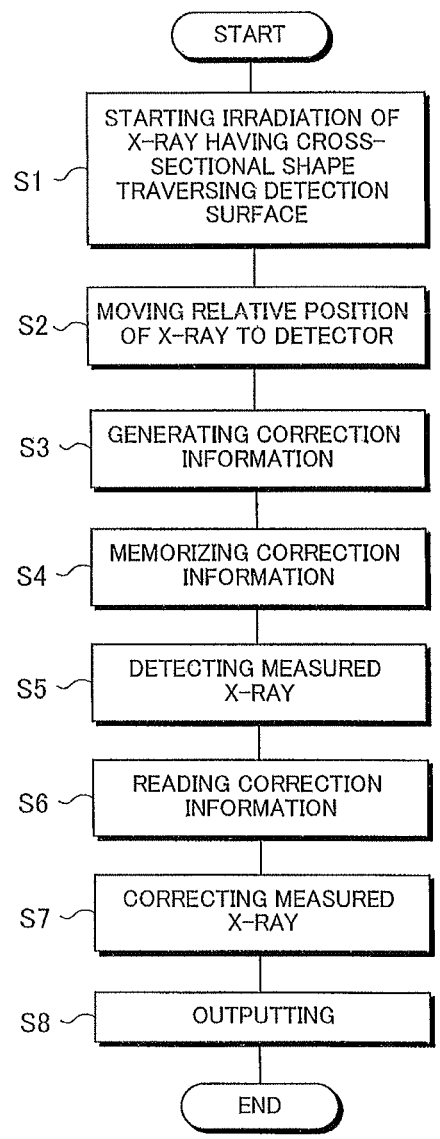
FIG. 3 is a flow chart illustrating a Flat-Field Correction method.

Using the configuration as mentioned above, Flat-Field Correction of X-ray detection sensitivity can be performed on the detector 130. FIG. 3 is a flow chart illustrating a Flat-Field Correction method. Initially, as illustrated in FIG. 3, irradiation of an X-ray having a cross-sectional beam shape traversing the detection surface to the detector 130 is started (Step S1). As in the above-mentioned case, it is preferable to use a diffraction X-ray as such an X-ray. This enables efficient Flat-Field Correction operation in a short time. The diffraction X-ray should not necessarily be used, instead, a direct beam limited by a slit may be used.

In a case where the detector 130 is irradiated with a diffraction X-ray, virtual flat-field irradiation using a uniform high-intensity X-ray is enabled. By irradiation of a high-intensity X-ray, more effective Flat-Field Correction operation is enabled in a short time. In addition, in this case, moving direction of the incident X-ray with respect to the detector 130 is the direction of the diffraction angle of a diffraction X-ray.

It is more preferable for a diffraction X-ray to be a Debye ring. In a case where the diffraction X-ray includes one diffracted by an oriented structure, the detector 130 cannot be irradiated with an X-ray that is uniform in a ring-shape. However, by use of a Debye ring, virtual flat-field irradiation using a uniform high-intensity X-ray having a cross-sectional beam shape traversing the detection surface is enabled. In a case where Flat-Field Correction is carried out using a diffraction X-ray of an oriented sample S instead of a Debye ring, since uniformity in a direction perpendicular to the moving direction (scanning direction) is not ensured by spherical correction only, it is preferable to carry out correction only for the moving direction.

The relative position of the detector 130 is moved with respect to the X-ray as mentioned above so that the whole of the detection surface is irradiated with the X-ray in total time (Step S2). At that time, the relative position of the X-ray with respect to the detector 130 is moved along the moving direction of the X-ray so that each pixel of the detector 130 is irradiated at the same integrated intensity. In addition, although in the above case of configuration, the detector 130 is moved, the X-ray beam source 110 may be moved. Even for a beam having any cross-sectional shape, by moving the detector by distance of three sheets of detection surfaces, uniform irradiation is enabled.

For example, if the detector 130 is moved to an X-ray having a cross-section of an arc shape, the arc will move the inside of the detection surface of the detector 130. By integrating irradiation amounts of the arc to the detection surface of the detector 130, irradiation amounts by the movement of the arc are integrated for all pixels. Flat-Field Correction is carried out using such integrated X-ray detection data. Further, it is also possible to determine a bad pixel from the obtained data.

Even in a case using a Debye ring, since X-ray intensity differs depending on the distance from the center to a measuring position, the number of counts tends to be large at the center and tends to be small at the both ends in the width direction of the detection surface. By carrying out spherical correction to intensity having such a difference, calculation can be carried out as uniform intensity. The spherical correction has a purpose to correct the influence that an X-ray originally having the same intensity on a sphere is extended by being projected on a plane.

In this way, based on the number of counts of X-rays detected for a given energy band, correction information for correcting the sensitivity of each pixel of the detector 130 is generated (Step S3). This enables easy Flat-Field Correction operation without special accessory equipment even with the X-ray diffractometer 100 already used by a user.

In a case where flat-field irradiation is carried out using an X-ray having a different energy, an X-ray in a constant energy band, for example, (Mo) X-ray, may be used. However, in a case of using a direct beam from the X-ray beam source 110, the detector 130 side may be adjusted so as to detect intensity for a specific energy band only.

In addition, as for the correction information, it is preferably a table including a correction coefficient of each of the pixels. This enables sensitivity correction for every pixel in an easy way by reading the table and multiplying it by detected intensity.

Next, information for correcting the sensitivity of each pixel of the detector 130 is generated under an assumption that each pixel arranged along the moving direction is irradiated with an X-ray at uniform integrated intensity. This enables sensitivity correction for every pixel in a simple way without carrying out spherical correction. In addition, such an operation can be performed by the correction information generation apparatus 200 connected to the X-ray diffractometer 100.

In addition, in case of using a Debye ring as an X-ray to be irradiated to the detector 130, it is preferable to generate the information for correcting the sensitivity of each pixel of the detector 130 under an assumption that the number of counts of detected X-rays is spherically corrected and the whole of the detection surface is irradiated at uniform integrated intensity. This enables more precise correction using the whole of the detection surface. Furthermore, as the distance from the sample S to the detector 130 becomes longer, spherical correction will not be in need.

The correction information generated as mentioned above is memorized on the correction information memory section 240 (Step S4). Upon detection of a diffraction X-ray in an experiment (Step S5), the memorized correction information is read out (Step S6), and correction is carried out by applying the information to the detected X-ray (Step S7). Then, corrected X-ray diffraction pattern image is outputted to an outside (Step S8). In this way, errors in X-ray counts can be corrected.

In addition, by carrying out measurement under the same condition and comparing the result with the sensitivity of former measurement, temporal change of the sensitivity can also be confirmed. In this case, whether the X-ray beam source 110 or the detector 130 is degraded or not is determined by whether the corrected average intensity (instead of the correction coefficient) exceeds a given reference value or not. The average intensity is memorized together with the correction coefficient when the correction coefficient is calculated.

Working Example

Figure 4:
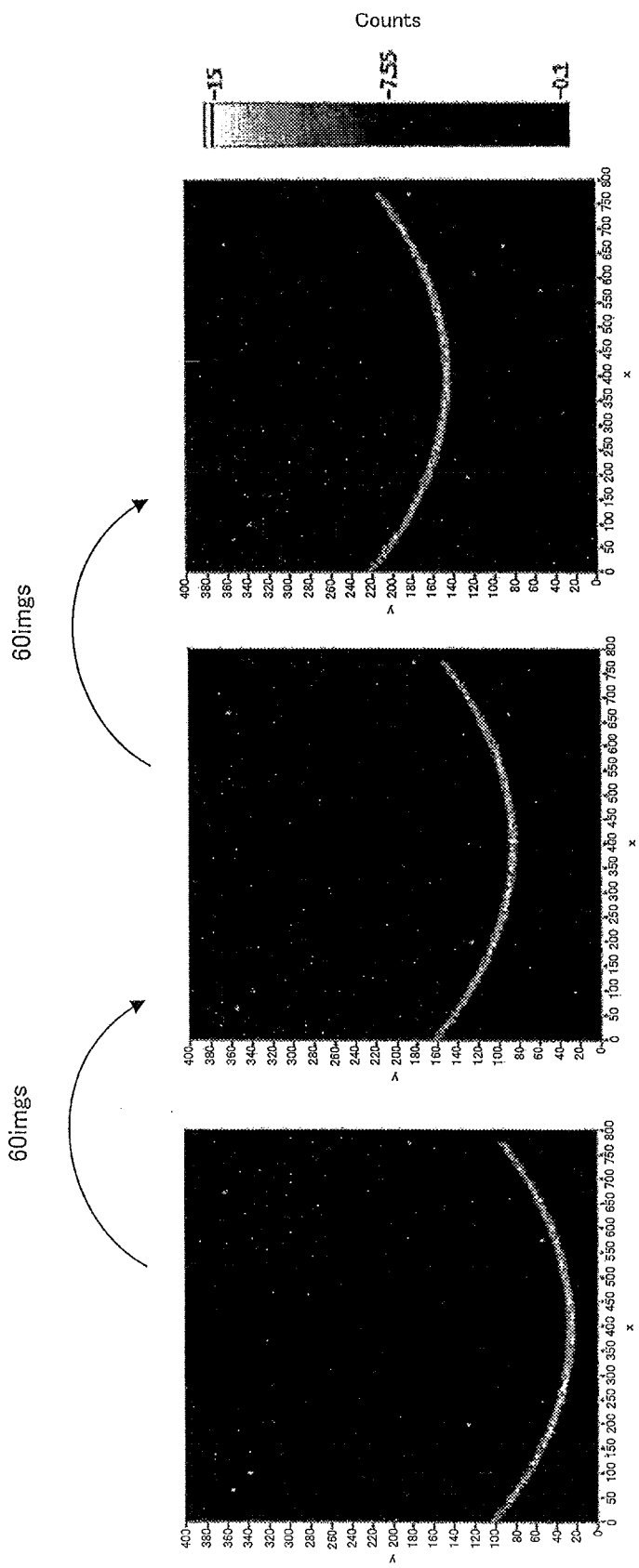
FIG. 4 is a view illustrating images in which a Debye ring is detected in each time.

The present inventors carried out a virtual flat-field irradiation experiment using the X-ray diffractometer 100 as mentioned above and confirmed that correction information for carrying out Flat-Field Correction can be generated. Initially we recorded an X-ray shot while moving the detector 130 with respect to a Debye ring. Shooting was carried out by moving the detector 130 provided with a chip module subjected to Flat-Field Correction at a constant speed. In this way, total 506 images were shot. FIG. 4 is a view illustrating images where a Debye ring is detected every 60 sheets from the 130th sheet, respectively. In the figure, a part having low density indicates the number of counts of each pixel. It is seen that the position of a Debye ring is shifted on a y-axis depending on the number of sheets.

Figure 5:
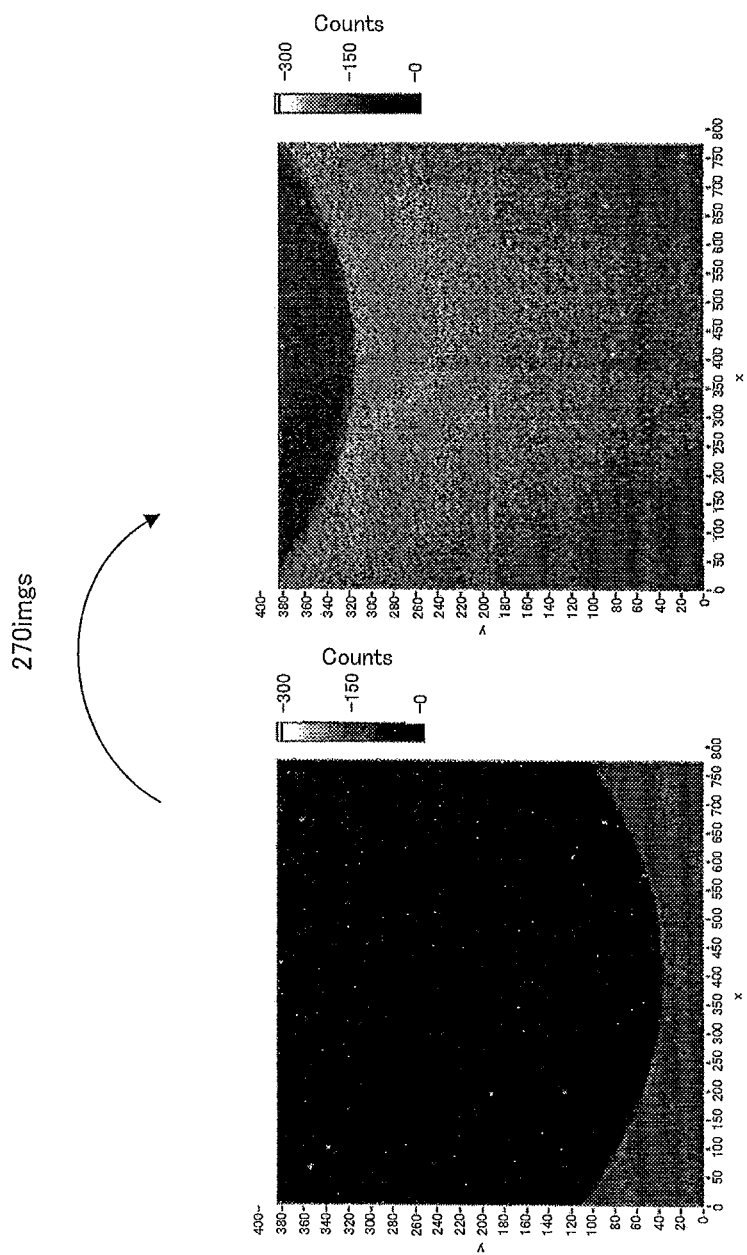
FIG. 5 is a view illustrating images in which integrated counts are recorded, respectively.

FIG. 5 is a view illustrating images on which the integrated counts are recorded up to 150th sheet, and 420th sheet, respectively. It is common to FIG. 4 in that a part having low density indicates the number of counts of each pixel. The total number of counts of each pixel is calculated. In FIG. 5, integrated counts of the right side image are not integrated to the end, but, it is seen that a very uniform image is recorded by integrating the number of counts in a y-axis direction in the figure. In the images of FIG. 5, background is not subtracted, thus, the influence of the background due to scattering appears as the position approaches closer to the center side of a direct beam.

Figure 6:
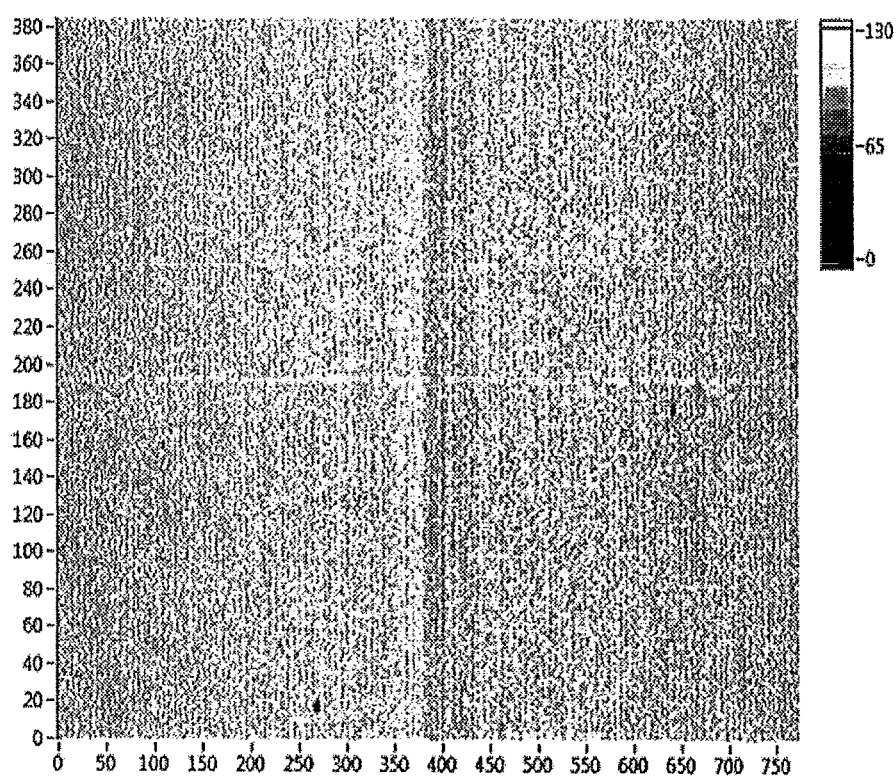
FIG. 6 is a view illustrating an image in which total integrated counts subtracted by counts due to scattering are recorded.

FIG. 6 is a view illustrating an image on which total integrated counts subtracted by counts due to scattering are recorded. In order to eliminate the counts due to scattering, by specifying an image of the maximum number of counts for each pixel, total counts of 10 sheets before the image and 10 sheets after the image were calculated. This represents the result where only values of pixel affected by a diffraction X-ray are integrated. Although some unevennesses of integrated counts are seen near the center of an x-direction, integrated counts are uniform at least in a y-direction that is the moving direction.

Figure 7A:
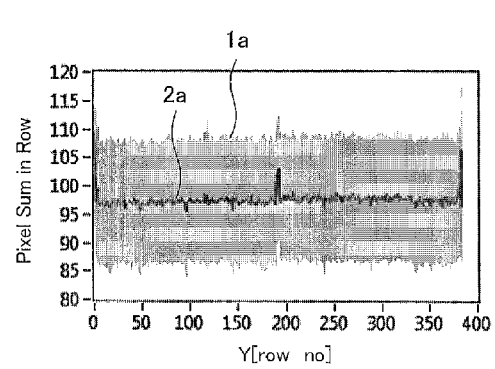
FIG. 7A is a graph illustrating distribution of counts in a moving direction.
Figure 7B:
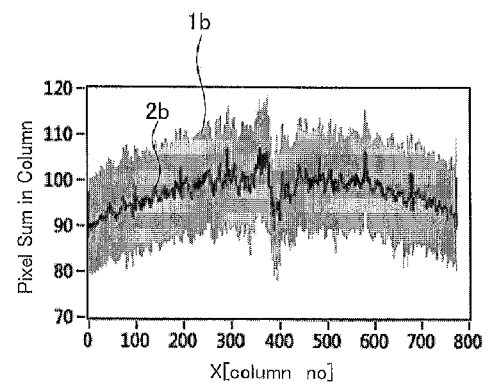
FIG. 7B is a graph illustrating the average value of integrated counts in a direction perpendicular to the moving direction.
Figure 8:
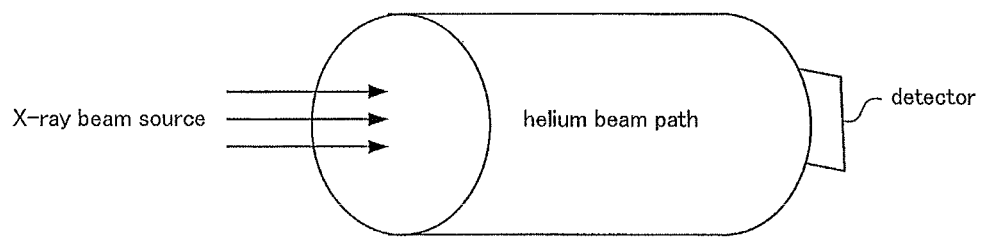
FIG. 8 is a schematic perspective view illustrating a conventional sensitivity correction method of a detection pixel.

FIG. 7A is a graph illustrating the distributions 1a and 2a of counts in the moving direction, and FIG. 7B is a graph illustrating the average values 1b and 2b of integrated counts in a direction perpendicular to the moving direction. These illustrate the results representing uniformity of the number of counts in x and y directions of the detector.

In the result illustrated in FIG. 7A, the average value is about 98 counts, thus, a sharp change is not seen in the average value 2a of the number of counts along the y-direction. In the result illustrated in FIG. 7B, the average value 2b decreases depending on the distance from the center of the detector 130. Such a tendency can be removed by spherical correction depending on the distance from the sample S to the detector 130. In addition, a sharp change is seen at the center toward the x-direction, which arises due to unevenness of a Debye ring. Such unevenness can be improved by, for example, rotating the powder sample S. As described above, it can be demonstrated that correction information for Flat-Field Correction can be generated using a Debye ring.

What is claimed is:

1. A correction information generation method for performing Flat-Field Correction of X-ray detection sensitivity on a pixel detector, comprising the steps of:
    moving a relative position of a detector with respect to an incident X-ray having a cross-sectional beam shape traversing a detection surface so that the whole of the detection surface is irradiated with the incident X-ray in total time and each of pixels arranged in a moving direction is uniformly irradiated; and
    generating information for correcting the sensitivity of a pixel based on an intensity value detected for a given energy band of the incident X-ray,
    wherein the incident X-ray is a diffraction X-ray; and
    the relative moving direction of the detector with respect to the incident X-ray is a diffraction angle direction of the diffraction X-ray.

2. The correction information generation method according to claim 1, wherein the incident X-ray is a Debye ring.

3. The correction information generation method according to claim 1, wherein the information for correcting the sensitivity of the pixel is generated under an assumption that each of the pixels arranged in the moving direction is irradiated at uniform integrated intensity.

4. The correction information generation method according to claim 1, wherein the information for correcting the sensitivity of the pixel is generated under an assumption that the detected intensity value is spherically corrected and the whole of the detection surface is irradiated at uniform integrated intensity.

5. The correction information generation method according to claim 1, wherein the information for correcting the sensitivity of the pixel is a table including a correction coefficient for each of the pixels.

6. A correction information generation apparatus for performing Flat-Field Correction of X-ray detection sensitivity on a pixel detector, the apparatus comprising
    a correction information generation section that generates information for correcting the sensitivity of a pixel based on a detected intensity value for a given energy band of an incident X-ray by moving a relative position of a detector with respect to the incident X-ray having a cross-sectional beam shape traversing a detection surface so that the whole of the detection surface is irradiated with the incident X-ray in total time and each of pixels arranged in a moving direction is uniformly irradiated, wherein the incident X-ray is a diffraction X-ray; and the relative moving direction of the detector with respect to the incident X-ray is a diffraction angle direction of the diffraction X-ray.

7. A correction information generation method for performing Flat-Field Correction of X-ray detection sensitivity on a pixel detector, comprising the steps of:

moving a relative position of a detector with respect to an incident X-ray having a cross-sectional beam shape traversing a detection surface so that the whole of the detection surface is irradiated with the incident X-ray in total time and each of pixels arranged in a moving direction is uniformly irradiated;

generating information for correcting the sensitivity of a pixel based on an intensity value detected for a given energy band of the incident X-ray; and wherein the information for correcting the sensitivity of the pixel is generated under an assumption that the detected intensity value is spherically corrected and the whole of the detection surface is irradiated at uniform integrated intensity.

* * * * *